(12) United States Patent
Hobbs

(10) Patent No.: US 7,145,038 B1
(45) Date of Patent: Dec. 5, 2006

(54) ALKYLATION OF A DIPHENYLAMINE COMPOUND IN IONIC LIQUID

(75) Inventor: Steven J. Hobbs, Wolcott, CT (US)

(73) Assignee: Chemtura Corporation, Middlebury, CT (US)

(*) Notice: Subject to any disclaimer, the term of this patent is extended or adjusted under 35 U.S.C. 154(b) by 0 days.

(21) Appl. No.: 11/304,163

(22) Filed: Dec. 14, 2005

(51) Int. Cl.
*C07C 2099/00* (2006.01)
(52) U.S. Cl. .................................................. 564/409
(58) Field of Classification Search ................ 564/409
See application file for complete search history.

(56) References Cited

U.S. PATENT DOCUMENTS

| 2,943,112 | A | 6/1960 | Popoff et al. ............... 260/576 |
|---|---|---|---|
| 4,824,601 | A | 4/1989 | Franklin .................... 252/401 |
| 4,973,759 | A | 11/1990 | Klein et al. ................. 564/437 |
| 5,214,211 | A | 5/1993 | Kurek et al. ................ 564/409 |
| 5,232,614 | A | 8/1993 | Colclough et al. ......... 252/32.7 |
| 5,672,752 | A | 9/1997 | Lai et al. .................... 564/409 |
| 5,734,084 | A | 3/1998 | Zhu ........................... 564/409 |
| 5,750,787 | A | 5/1998 | Lai et al. .................... 564/409 |
| 6,315,925 | B1 | 11/2001 | Aebli et al. ................ 252/401 |

FOREIGN PATENT DOCUMENTS

| EP | 0 807 620 | 11/1997 |
|---|---|---|
| GB | 2 325 929 | 12/1998 |
| JP | 55-053249 | 4/1980 |

OTHER PUBLICATIONS

Parkinson, "Ionic Liquids Make an Environmental Splash,"100 *Chemical Engineering Progress* 7 (Sep. 2004).

Venuto et al., "Organic Reactions Catalyzed by Crystalline Aluminosilicates" 4 *Journal of Catalysis* 81-98 (1966).

Holbrey, "Industrial Applications of Ionic Liquids," *Chemistry Today* 35 (Jun. 2004).

Wilkes, "Friedel-Crafts Reactions in Chloroaluminate Molten Salts," *Molten Salt Chemistry: An Introduction and Selected Applications* 405 (Mamantov and Marassi Eds. 1987).

Nelson, "Are Ionic Liquids Green Solvents?" 818 *ACS Symposium Series* 30-41, (American Chemical Society 2002).

Davis et al., "Synthesis and Purification of Ionic Liquids," *Ionic Liquids in Synthesis* 7 (Wasserschied & Welton Eds. 2003).

Anthony et al., "Physicochemical Properties of Ionic Liquids," *Ionic Liquids in Synthesis* 41 (Wasserschied & Welton Eds. 2003).

Earle et al, "Organic Synthesis," *Ionic Liquids in Synthesis* 174 (Wasserschied & Welton Eds. 2003).

Drake et al., "Structural Effects on the Physical Properties of Ionic Liquids," *Air Force Research Laboratory Report No.* AFRL-PR-ED-VG-2003-122 (May 2003).

"BASIL™—First Commercial Process Using Ionic Liquids" *Chemicals Research and Engineering* http://www.corporate.basf.com/en/innovationen/labors/chemikalien, (Mar. 2003).

Boswell, "Technology Watch: Ionic Liquids Offer New Solutions" *Chemical Market Reporter* FR14-16 (Jan. 2004).

Freemantle, "Designer Liquids in Polymer Systems" *Chemical and Engineering News* 26-29 (May 2004).

*Primary Examiner*—Samuel Barts
(74) *Attorney, Agent, or Firm*—Michael P. Dilworth

(57) ABSTRACT

A process for alkylation of a diphenylamine compound in an ionic liquid. The use of an ionic liquid permits convenient separation of the alkylated reaction product from the reaction mixture.

20 Claims, No Drawings

ALKYLATION OF A DIPHENYLAMINE COMPOUND IN IONIC LIQUID

BACKGROUND OF THE INVENTION

The present invention relates to the alkylation of a diphenylamine compound. Alkylated diphenylamines have utility as antioxidants in lubricants, rubber compositions and plastics.

The prior art has sought to improve the alkylation of diphenylamine. For example, U.S. Pat. No. 2,943,112 discloses the purification of the crude alkylate by subsequent, selective alkylation of unreacted diphenylamine with certain olefins. U.S. Pat. No. 5,214,211 discloses rare earth pillared clays as catalysts for the alkylation of diphenylamine compounds. Other attempts to enhance the production of desirable monoalkylated diphenylamine and reduce the amount of unreacted diphenylamine reactant and undesirable dialkylated diphenylamine product are reported in U.S. Pat. Nos. 5,750,787 and 6,315,925.

An ionic liquid consists of inorganic and/or organic cations and anions, and typically has a very low vapor pressure, a wide liquid temperature range, and is non-flammable. Ionic liquids can act as a catalyst and/or solvent, and have been studied for utility as solvents, electrolytes, in separations and in fluid applications such as lubricants. See Holbrey, "Industrial Applications of Ionic Liquids," *Chemistry Today* 35 (June 2004); Parkinson, "Ionic Liquids Make an Environmental Splash," 100 *Chemical Engineering Progress* 7 (September 2004); and Drake et al., "Structural Effects on the Physical Properties of Ionic Liquids," *Air Force Research Laboratory Report No. AFRL-PR-ED-VG-2003-12* (May 2003).

The use of ionic liquids in Friedel-Crafts alkylation has been discussed in Wilkes, "Friedel-Crafts Reactions in Chloroaluminate Molten Salts," *Molten Salt Chemistry: An Introduction and Selected Applications* 405 (Mamantov and Marassi Eds. 1987) and Earle et al., "Organic Synthesis," *Ionic Liquids in Synthesis* 174 (Wasserschied & Welton Eds. 2003). However, neither study is directed to an alkylation reaction of a phenyl ring of a diphenylamine compound.

An object of the invention is to provide a synthesis which permits alkylation of a phenyl ring of a diphenylamine compound.

A feature of the invention is the use of an ionic liquid as a solvent and catalyst for the alkylation reaction.

An advantage of the invention is that use of an ionic liquid typically permits convenient separation of the alkylated diphenylamine compound(s) from the reaction mixture.

BRIEF SUMMARY OF THE INVENTION

In one aspect, the present invention relates to a process for alkylating a phenyl ring of a diphenylamine compound, comprising reacting a diphenylamine compound with an alkylating agent in the presence of an ionic liquid comprising a Lewis acid anion and a quaternary cation, to produce an alkylated diphenylamine compound.

DETAILED DESCRIPTION OF THE PREFERRED EMBODIMENTS

As summarized above, the present invention relates to the alkylation of a phenyl ring of a diphenylamine compound in the presence of an ionic liquid. By "diphenylamine compound" it is meant unsubstituted diphenylamine and substituted diphenylamine compounds in which at least one phenyl ring has at least one substituent.

The alkylating agent may be a substituted or unsubstituted linear, branched or cyclic olefin or an arylalkene. Suitable linear olefins include 1-hexene, 1-nonene, 1-decene and 1-dodecene. Suitable cyclic olefins include cyclohexene, cyclopentene and cyclooctene. Suitable branched olefins include propylene trimer (nonenes), propylene tetramer (dodecenes), propylene pentamer and diisobutylene. Suitable arylalkylenes include styrene, methyl styrene, 3-phenylpropene and 2-phenyl-2-butene.

The ionic liquid may be composed entirely of anions and cations, and may conveniently be prepared by mixing together a Lewis acid and an alkyl quaternary metal salt, preferably under heat.

The Lewis acid may be a metal halide, an alkyl halide, an alkylaryl halide, or an alkyl sulfonate ester such as an alkyl tosylate, an alkyl mesylate or an alkyl triflate. Suitable Lewis acid metal halides include aluminum chloride, aluminum bromide, indium trichloride, gallium trichloride, niobium pentachloride, tantalum pentachloride, titanium tetrachloride, boron trifluoride, boron trifluoride etherate, boron trichloride, ferric chloride, and zirconium chloride. Illustrative alkyl halides include methyl chloride, methyl bromide, methyl iodide, ethyl chloride, ethyl bromide, ethyl iodide, n-propyl chloride, n-propyl bromide, n-propyl iodide, isopropyl chloride, isopropyl bromide, isopropyl iodide, n-butyl chloride, n-butyl bromide, n-butyl iodide, isobutyl chloride, isobutyl bromide, isobutyl iodide, tert-butyl chloride, tert-butyl bromide, tert-butyl iodide, n-pentyl chloride, n-pentyl bromide, n-pentyl iodide, neopentyl bromide, neopentyl chloride, neopentyl iodide, octyl chloride, octyl bromide and octyl iodide. Illustrative alkylaryl halides include benzyl bromide, benzyl chloride, benzyl iodide, $\alpha$-phenylethyl chloride, $\alpha$-phenylethyl bromide, $\alpha$-phenylethyl iodide, $\beta$-phenylethyl chloride, $\beta$-phenylethyl bromide and $\beta$-phenylethyl iodide.

The alkyl quaternary metal salt may be a quaternary ammonium salt, an alkylphosphonium salt, an alkylimidazolium salt, an alkyltriazolium salt and an alkylpyridinium salt. Suitable quaternary ammonium salts may be based on cations selected from the group consisting of benzyltrimethylammonium, butyltrimethylammonium, methyltriethylammonium, ethyltrimethylammonium, tetra-n-butylammonium, n-hexyl-trimethylammonium, n-heptyl-trimethylammonium, n-octyl-trimethylammonium, n-hexyl-triethylamonium, n-heptyl-triethylammonium, n-octyl-triethylammonium, n-hexyl-tri-n-butylammonium, n-heptyl-tri-n-butylammonium, n-octyl-tri-n-butylammonium, tris-(n-propyl)-undecylammonium, tetra-n-pentylammonium, n-decyl-n-octyl-dimethylammonium and n-tetradecyl-triethylammonium.

Suitable alkylphosphonium salts may be based on cations selected from the group of benzyltrimethylphosphonium, butyltrimethylphosphonium, methyltriethylphosphonium, ethyltrimethylphosphonium, tetra-n-butylphosphonium, n-hexyl-trimethylphosphonium, n-heptyl-trimethylphosphonium, n-octyl-trimethylphosphonium, n-hexyl-triethylphosphonium, n-heptyl-triethylphosphonium, n-octyl-triethylphosphonium, n-hexyl-tri-n-butylphosphonium, n-heptyl-tri-n-butylphosphonium, n-octyl-tri-n-butylphosphonium, tris-(n-propyl)-undecylphosphonium, tetra-n-pentylphosphonium, N-decyl-n-octyl-dimethylphosphonium and N-tetradecyl-triethylphosphonium.

Suitable alkylimidazolium salts may be based on cations selected from the group consisting of 1-methyl-3-methylimidazolium, 1-ethyl-3-methyl-imidazolium, 1-butyl-3- methylimidazolium, 1-dodecyl-5-methylimidazolium, 1-(2, 2,2-trifluoroethyl)-3-methylimidazolium, 1-(ethoxymethyl)-3-methyl imidazolium, 3-ethyl-1-ethylimidazolium, 3-ethyl-1-butyl-imidazolium, 1-ethyl-2,3-dimethyl-imidazolium, 1,2-diethyl-3-methylimidazolium, 1-ethyl-3,5-dimethyl-imidazolium and 1,3-diethyl-5-methylimidazolium.

Suitable alkyltriazonium salts may be based on cations selected from the group consisting of 1-(3',3',3'-trifluoro-n-propyl)-3-n-butyl-1,2,4-triazolium, 1-(2'-fluoroethyl)-3-n-heptyl-1,2,4-triazolium, 1-(2'-fluoroethyl)-3-n-decyl-1,2,4-triazolium, 1-(1H,1H,2H,2H-perfluoro-n-hexyl)-3-n-butyl-1,2,4-triazolium, 1-n-propyl-4-amino-1,2,4-triazolium, 1-n-butyl-4-amino-1,2,4-triazolium and 1-n-hexyl-4-amino-1,2, 4-triazolium.

In a preferred embodiment, the ionic liquid is formed in situ prior to addition of the alkylating agent. The Lewis acid alkyl quaternary metal salt and N'-phenyl-N-alkylphenylenediamine may be added to a suitable reaction vessel, preferably under a dry, inert atmosphere and with heating to a temperature up to 200° C., and stirred, for example at 200 to 300 rpm, until an ionic liquid phase and an organic phase are formed. The inert atmosphere serves to protect the ionic liquid from oxidation, and is preferably selected from the group consisting of argon, helium and nitrogen. The inert atmosphere should also be dry to avoid decomposition of the ionic liquid.

The alkylating agent may be added to the reaction vessel once the two phases have been formed, either all at once or by multiple partial additions.

The alkylation reaction may preferably be performed at a temperature of from 80 to 200° C. over a time period of from 1 to 24 hours.

The alkylation reaction produces a mixture of mono, di and tri-alkylated diphenylamines. The reaction products may be separated from the reactants by conventional separation techniques and apparatus such as a separatory funnel well known to one of ordinary skill in the art. Similarly, the isolated reaction mixture may be separated into its component compounds using conventional separation techniques and apparatus well known to those of ordinary skill in the art, such as, for example, high pressure liquid chromatography.

EXAMPLES

The following Examples illustrate the practice and advantages of the invention in greater detail with respect to individual species thereof. The details of the examples are illustrative only, and are not to be used to constrict the scope of the claims.

Example 1

Alkylation of Diphenylamine Using Nonene, Aluminum Chloride and 1-butyl-3-methyl-imidazolium chloride A 1-L flask equipped with a mechanical stirrer, pressure equilibrated dropping funnel, thermocouple, temperature controller, heating mantle and inlet for nitrogen positive pressure was charged with 84.68 g diphenylamine (0.50 mole) and a first portion of nonenes (75.81 g, 0.60 mole), followed by 20.04 g aluminum chloride powder (0.15 mole, 30 mole % relative to diphenylamine) and then 17.59 g of solid 1-butyl-3-methyl-imidazolium chloride (0.10 mole). The mixture was warmed to 75° C. with stirring (approximately 300 rpm). The aluminum chloride and 1-butyl-3-methyl-imidazolium chloride gradually formed a dense liquid phase which would settle to the bottom of the flask if stirring was stopped. The mixture was then warmed to 140° C. and a second portion of nonene (142.25 g, 1.15 mole) was added to the mixture over 1.5 h. When the addition is complete, the two-phase system was raised to 145° C. and held there for 5.2 hours.

The flask contents were permitted to cool to ambient temperature, and the reaction mixture was transferred to a 2-L separatory funnel. The lower phase, comprising the ionic liquid catalyst and having a very dark color, was separated. The upper, organic phase was diluted with 500 ml heptane, washed with 500 ml water, and then dilute aqueous ammonia (400 ml water, 100 ml conc. aq. ammonia), and then dried over anhydrous sodium sulfate. The drying agent was removed by suction filtration through a pad of Celite #208 over glass fiber filter paper (0.90 cm, 934 AH). The resulting filtrate was stripped under vacuum to obtain 176.55 g of a honey colored, viscous oil, which contained 0.4% unreacted diphenylamine, 13.6% monononyldiphenylamine, and 86.0% di- and tri-nonyldiphenylamine based on gas chromatographic analysis.

A comparable alkylation reaction performed using the same amount of aluminum chloride but without 1-butyl-3-methyl-imidazolium chloride produced 166.92 of product, which contained 5.5% unreacted diphenylamine, 35.4% monononyldiphenylamine and 58.9% dinonyldiphenylamine.

This data demonstrates the ionic liquid catalyzed alkylation produces a greater percentage of dialkylate than alkylation using aluminum chloride alone. This is an advantage because dialkylated diphenylamines are more desirable in lubricant compositions than monoalkylated diphenylamines.

Example 2

Alkylation of Diphenylamine Using Nonene, Aluminum Chloride and Tetrabutylammonium Bromide A 1-L, 4 necked round bottom flask equipped with a pressure-equilibrated dropping funnel, mechanical stirrer, reflux condenser topped with a nitrogen line for positive pressure, temperature controller, thermocouple and heating mantle was charged in succession with 84.66 g (0.50 mole) of solid diphenylamine, a first portion (75.74 g; 0.60 mole) of nonene, 20.08 g (0.15 mole, 30 mole % relative to the diphenylamine) of aluminum chloride, and 32.27 g (0.10 mole, 20 mole % relative to the diphenylamine) of tetrabutylammonium bromide. The resulting slurry was stirred at approximately 300 rpm and warmed under nitrogen to a target temperature of 140° C., upon which two phases began to form: a lower, low volume dark catalyst phase, and a lighter organic phase. The second portion of nonenes (145.25 g, 1.15 mole) was then added over 1.5 h. The temperature was then raised to 145° C. and held there for 5.2 h. 5 ml aliquots of the reaction mixture were taken at the 2 hr and 5.2 h points, and were kept cold for later GC analysis.

The product was isolated by permitting the reaction mixture to cool to room temperature, which solidified the lower catalyst phase into a dark crystalline mass. The lighter colored product phase was decanted off and the catalyst mass washed in the flask with 100 ml n-heptane. The organic phases were combined in a 2-L separatory funnel, washed twice with 500 ml water and then diluted ammonia (400 ml water, 100 ml conc. aq. ammonia) prior to drying over anhydrous sodium sulfate. The sodium sulfate was removed by suction filtration through 934 AH glass fiber filter paper and the filtrate condensed on a rotary evaporator in vacuo (95° C., <5 mm final vacuum). This procedure removed most of the residual nonenes and the n-heptane. 180.91 g of yellow-brown viscous oil was obtained, which comprised 0.5% unreacted diphenylamine, 13.2% combined monononyl diphenylamines, 79.5% dinonyldiphenylamines and 6.1% trinonyldiphenylamines, based on gas chromatographic analysis.

The inventors currently believe the ionic liquid may be recycled for use in subsequent alkylations by simple phase separation in which the hydrocarbon-soluble reaction product(s) is/are decanted, and thus separated from, the denser aluminum chloride-based ionic liquid phase. The ionic liquid may then be used to catalyze another alkylation reaction by itself, or in combination with fresh catalyst.

I claim:

1. A process for alkylating a phenyl ring of a diphenylamine compound, comprising reacting a diphenylamine compound with an alkylating agent in the presence of an ionic liquid comprising a Lewis acid and a quaternary cation, to produce an alkylated diphenylamine compound.

2. The process of claim 1, wherein said diphenylamine compound is unsubstituted diphenylamine.

3. The process of claim 1, wherein said diphenylamine compound has at least one substituent on at least one phenyl ring.

4. The process of claim 1, wherein said alkylating agent is a substituted or unsubstituted linear, branched or cyclic olefin or an arylalkene.

5. The process of claim 4, wherein said olefin is a linear olefin selected from the group consisting of 1-hexene, 1-nonene, 1-decene and 1-dodecene.

6. The process of claim 4, wherein said olefin is a branched olefin selected from the group consisting of propylene trimer, propylene tetramer, propylene pentamer and diisobutylene.

7. The process of claim 4, wherein said olefin is a cyclic olefin selected from the group consisting of cyclohexene, cyclopentene and cycloctene.

8. The process of claim 4, wherein said olefin is an arylalkene selected from the group consisting of styrene, methyl styrene, 3-phenylpropene and 2-phenyl-2-butene.

9. The process of claim 1, wherein said Lewis acid is a metal halide selected from the group consisting of aluminum chloride, aluminum bromide, indium trichloride, gallium trichloride, niobium pentachloride, tantalum pentachloride, titanium tetrachloride, boron trifluoride, boron trichloride etherate, ferric chloride, and zirconium chloride.

10. The process of claim 1, wherein said Lewis acid is an alkyl halide selected from the group consisting of methyl chloride, methyl bromide, methyl iodide, ethyl chloride, ethyl bromide, ethyl iodide, n-propyl chloride, n-propyl bromide, n-propyl iodide, isopropyl chloride, isopropyl bromide, isopropyl iodide, n-butyl chloride, n-butyl bromide, n-butyl iodide, isobutyl chloride, isobutyl bromide, isobutyl iodide, tert-butyl chloride, tert-butyl bromide, tert-butyl iodide, n-pentyl chloride, n-pentyl bromide, n-pentyl iodide, neopentyl bromide, neopentyl chloride, neopentyl iodide, octyl chloride, octyl bromide and octyl iodide.

11. The process of claim 1, wherein said Lewis acid is an alkylaryl halide selected from the group consisting of benzyl bromide, benzyl chloride, benzyl iodide, α-phenylethyl chloride, α-phenylethyl bromide, α-phenylethyl iodide, β-phenylethyl chloride, β-phenylethyl bromide and β-phenylethyl iodide.

12. The process of claim 1, wherein said Lewis acid is an alkyl sulfonate ester.

13. The process of claim 1, wherein said quaternary cation is selected from a quaternary ammonium cation, an alkylphosphonium cation, an alkylimidazolium cation, an alkyltriazolium cation and an alkylpyridinium cation.

14. The process of claim 13, wherein said quaternary ammonium cation is a member selected from the group consisting of benzyltrimethylammonium, butyltrimethylammonium, methyltriethylammonium, ethyltrimethylammonium, tetra-n-butylammonium, n-hexyl-trimethyla monium, n-heptyl-trimethylammonium, n-octyl-trimethylammonium, n-hexyl-triethylamonium, n-heptyl-triethylammonium, n-octyl-triethylammonium, n-hexyl-tri-n-butylamonium, n-heptyl-tri-n-butylammonium, n-octyl-tri-n-butylammonium, tris-(n-propyl)-undecylammonium, tetra-n-pentylammonium, n-decyl-n-octyl-dimethylammonium and n-tetradecyl-triethylammonium.

15. The process of claim 13, wherein said alkylimidazolium cation is a member selected from the group consisting of 1-methyl-3-methyl-imidazolium, 1-ethyl-3-methyl-imidazolium, 1-butyl-3-methylimidazolium, 1-dodecyl-5-methylimidazolium, 1-(2,2,2-trifluoroethyl)-3-methylimidazolium, 1-(ethoxymethyl)-3-methylimidazolium, 3-ethyl-1-ethylimidazolium, 3-ethyl-1-butyl-imidazolium, 1-ethyl-2,3-dimethyl-imidazolium, 1,2-diethyl-3-methylimidazolium, 1-ethyl-3,5-dimethyl-imidazolium and 1,3-diethyl-5-methylimidazolium.

16. The process of claim 13, wherein said alkyltriazolium cation is a member selected from the group consisting of 1-(3',3',3'-trifluoro-n-propyl)-3-n-butyl-1,2,4-triazolium, 1-(2'-fluoroethyl)-3-n-heptyl-1,2,4-triazolium, 1-(2'-fluoroethyl)-3-n-decyl-1,2,4-triazolium, 1-(1H,1H,2H,2H-perfluoro-n-hexyl)-3-n-butyl-1,2,4-triazolium, 1-n-propyl-4-amino-1,2,4-triazolium, 1-n-butyl-4-amino-1,2,4-triazolium and 1-n-hexyl-4-amino-1,2,4-triazolium.

17. The process of claim 1, wherein said ionic liquid is formed is formed in situ prior to addition of said alkylating agent.

18. The process of claim 1, performed at a temperature of from 80 to 200° C. over a time period of from 1 to 24 hours.

19. The process of claim 1, performed under an inert atmosphere selected from the group consisting of argon, helium and nitrogen.

20. The process of claim 1, performed with stirring at a stirring speed of from 200 to 300 rpm.

* * * * *